United States Patent [19]
Hollander et al.

[11] Patent Number: 4,670,468
[45] Date of Patent: Jun. 2, 1987

[54] METHOD FOR PROTECTING AND HEALING GASTRODUODENAL MUCOSA AND THE LIVER OF MAMMALS

[75] Inventors: Daniel Hollander, Newport Beach; Andrzej S. Tarnawski, Costa Mesa, both of Calif.

[73] Assignee: Regents of the University of California, Berkeley, Calif.

[21] Appl. No.: 684,507

[22] Filed: Dec. 21, 1984

Related U.S. Application Data

[60] Division of Ser. No. 515,766, Jul. 21, 1983, abandoned, which is a continuation-in-part of Ser. No. 406,558, Aug. 9, 1982, abandoned.

[51] Int. Cl.$^4$ ............................................... A61K 31/20
[52] U.S. Cl. .................................... 514/560; 514/893; 514/894; 514/926
[58] Field of Search ................. 514/560, 893, 894, 926

[56] References Cited

U.S. PATENT DOCUMENTS 4,388,324  6/1983  Horrobin ............................. 424/318

OTHER PUBLICATIONS

Husa's-*Pharmaceutical Dispensing*, Martin, Mack Pub. Co., Easton, PA (1966) pp. 177–179.
*Cecil Textbook of Medicine*, Sixteenth Edition, W. B. Saunder Company, p. 2022.

*Primary Examiner*—Frederick E. Waddell
*Attorney, Agent, or Firm*—Poms, Smith, Lande & Rose

[57] ABSTRACT

A method is disclosed for protecting or healing of the mammalian gastro-duodenal mucosa by employing arachidonic acid or linoleic acid and a pharmaceutically acceptable water solubilizing surface active agent therefor.

5 Claims, No Drawings

METHOD FOR PROTECTING AND HEALING GASTRODUODENAL MUCOSA AND THE LIVER OF MAMMALS

REFERENCE TO CROSS RELATED APPLICATIONS

This application is a divisional Application of U.S. patent application Ser. No. 06/515,766, filed July 21, 1983, now abandoned, which in turn is a continuation-in-part Application of U.S. patent application Ser. No. 406,558 filed Aug. 9, 1982, now abandoned.

BACKGROUND OF THE INVENTION

Ethanol, aspirin and taurocholic acid, a component of bile, may cause severe injury to the gastro-duodendal mucosa of mammals, including experimental animals (e.g. rats) and humans, when these three agents separately or in conjunctions come in contact with the gastro-duodendal mucosa. The injuries to the gastro-duodendal mucosa caused by these three substances which have been documented in various respected clinical journals, include the following: acute hemorrhagic gastritis with acute upper gastro-intestinal bleeding; gastric erosions and ulcer formation (particularly related to aspirin and taurocholic acid); and alkaline reflux syndrom occurring spontaneously or after gastric surgery.

Ethanol, in addition to causing injury to the gastro-duodendal mucosa, also produces severe injury to the liver in mammals, when ingested by said mammal including humans, as documented by elevation of certain serum enzymes and liver histology. Other hepatotoxic substances also produce liver damage.

Various prior art investigators have conducted a variety of experiments in an attempt to find a composition which will protect the gastro-duodenal mucosa and the liver from injury caused by ethanol and other toxic substances. It has been determined that various prostaglandins may prevent gastro-duodenal and liver injury produced by ethanol and other toxic substances. However, prostaglandins are expensive and have systemic side effects.

We have discovered that two relatively inexpensive fatty acids which are not only not harmful to the body but are necessary dietary substances will protect and/or heal the liver from injury induced by hepatotoxic substances and the gastro-duodenal mucosa from ethanol, aspirin and taurocholic acid induced injury. These two fatty acids are arachidonic acid and linoleic acid which are present, in relatively small amounts, in a normal diet. It is known that these two acids are precursors of prostaglandins. For example, previous in vitro studies have indicated that the gastric mucosa of various animals, including humans, is able to synthesize protaglandins (including prostaglandin $E_2$ and $F_2$) from arachiodonic acid when the stomach lining is ground up (including the mucosa) and the arachidonic acid mixed therewith. It is also known that arachidonic acid is converted to prostaglandin $E_2$ in the small intestine. However, when either arachidonic or linoleic acid are taken orally, either per se or in a food, they are not able to be absorbed by the gastro-duodenal mucosa and the arachidonic acid and linoleic acid which is absorbed by the small intestine distal to the duodenum and converted to protaglandin cannot reach the gastro-duodenal mucosa because they are metabolized and deactivated by the lungs. We have found that if these two acids are absorbed distal to the duodenum the two fatty acides have absolutely no effect on protecting and healing the gastro-duodenal mucosa or the liver.

SUMMARY OF THE INVENTION

The present invention is based on the surprising discovery that the oral administration, to mammals, of arachidonic and linoleic acids will protect and/or heal the liver from ethanol and other hepatotoxic substances and the gastro-duodenal mucosa from injury induced by ethanol, aspirin and taurocholic acid, if the arachidonic acid or linoleic acid is first mixed with a pharmaceutically acceptable water solubilizing compound which makes the fatty acid soluble in water and allows the fatty acids to be absorbed by the gastro-duodenal mucosa. We have found that when the fatty acid is absorbed by the mucosa, prostaglandins (e.g. prostaglandin $E_2$) are synthesized. We believe that this is what protects and/or heals the liver and the gastro-duodenal mucosa.

The water solubilizing compounds, which are also pharmaceutically acceptable, may be a variety of compounds providing that they will solubilize either of the fatty acids in an aqueous medium, such as the aqueous fluids secreted by the gastric and duodenal mucosa. The preferred water solubilizing compounds of the present invention are the non-ionic surface active agents such as ethylene oxide surface active agents; including polyethenoxy ethers of alkyl phenols, polyethenoxy ethers of alcohols, and polyethenoxy ethers of mercaptans; difunctional and polyfunctional polyethenoxy ethers (e.g. condensation of ethylene oxide with bis-phenols), polyethenoxy esters, particularly of tall oil acids as well as rosins and alkylated benzoic acid; polyethenoxy compounds with amide links, etc.

The concentration of the linoleic or arachidonic acid in the water solubilizing compound is not particularly important but we have found that, in general, the concentration will be between about 10 and 200 mM, and, preferably, the concentration is between about 30 or 60 mM and about 120 or 150 mM.

The dosages of the fatty acids of the present invention which are necessary to achieve the desired results can be determined by the art-skilled and, in general, a dosage of at least about 5 mg/kg will be used. There is no theoretical limit on the maximum amount although excellent results will be obtained using 75 or 100 mg/kg and therefore there is no reason to use higher dosages. The presently preferred dosages are between about 15 or 18 mg/kg and about 25 or 30 mg/kg.

We have also found that the fatty acids of the present invention may be administered many hours before the gastro-duodenal mucosa is contracted by one or more of the three potentially harmful agents and still protect the gastro-duodenal mucosa. We believe, for example, that the instant composition may be administered up to 3 hours prior to ingestion of any of the toxic substances and still protect the gastro-duodenal mucosa and the liver.

DESCRIPTION OF THE PREFERRED EMBODIMENTS

We have observed that in order to protect the liver and/or the gastro-duodenal mucosa it is necessary that the gastric mucosa absorb either the arachidonic acid or the linoleic acid, or mixtures of both. Either the liver or the jejunal portion of the small intestine will not protect the gastro-duodenal mucosa from the harmful effect of the three agents.

In order to more fully understand the present invention reference will be made to the following examples, which are for the purpose of illustration only and are not to be considered limiting.

In the following examples the water solubilizing compound was a non-ionic surfactant prepared by the addition of ethylene oxide to polypropylene glycol which is marketed under the trademark Pluronic F-68 (sometimes hereinafter abbreviated as PL). PL's CTFA name is Poloxamer 188. PL is a member of a family of block copolymers manufactured under the trademark Pluronic Polyols. PL contains 80 wt. % ethylene oxide and has a molecular weight of 8,350. In the examples or studies PL was used as a 5 mM solution in a saline solution of 0.9% sodium chloride adjusted to a pH of 8.0 with sodium hydroxide.

The arachidonic acid was a grade 1 acid which was stored in the dark at minus 20° C. in sealed ampules until used. When the ampule was opened the arachidonic acid was transferred immediately to a vial which was under a stream of nitrogen and contained the 5 mM PL saline solution. The mixture was stirred vigorously and the pH adjusted to 8.0 with sodium hydroxide. The resulting solution became optically clear and remained so for 24 hours. Arachidonic acid solutions of 30, 60 and 120 mM in 5 mM PL were prepared immediately prior to their administration to the animals.

The linoleic acid used in the subsequent examples was also solubilized in the 5 mM PL saline solution as indicated above.

The animals used in the examples were Sprague-Dawley rats (225 to 250 grams bodyweight). Twenty-four hours prior to the experimentation the animals were fasted in wire-bottomed cages to prevent coprophagy.

Study 1

Arachidonic acid mucosal protection for 3 hours after ethanol administration

Animals were given by gavage 1 ml of either saline, or 5 mM PL solution in saline, or 1 ml of the PL -saline solution containing arachidonic acid in 30, 60 and 120 mM concentrations respectively. One-half hour or 1 hour later, 2 ml of absolute ethanol were instilled into the stomach by gavage. Three hours later the animals were sacrificed and their stomachs removed.

Study 2

Arachidonic acid mucosal protection for 15 hours after ethanol administration

One ml of 120 mM arachidonic acid solution (37 mg arachidonic acid) or 5 mM PL solution was instilled into the stomach 1 hour prior to the intragastric administration of 2 ml ethanol. The animals were killed 15 hours after ethanol administration and their stomachs were examined.

Study 3

Intragastric versus intrajejunal administration of arachidonic acid

The next series of experiments was designed to compare the effect of intragastric to intrajejunal pretreatment with arachidonic acid on ethanol-induced gastric mucosal injury. The animals were anesthetized with nembutal (50 mg nembutal per kg body weight intraperitoneally), their abdomens were opened and either 1 ml of 120 mM arachidonic acid or 5 mM PL was instilled intragastrically or 1 ml of 120 mM arachidonic acid intrajejunally with a polyethylene catheter introduced through a small duodenal incision. The pylorus was ligated immediately after solution instillation. One hour later the gastric contents were removed and 2 ml of ethanol were instilled through the catheter. The stomach was examined 2 hours later.

Computerized analysis of mucosal changes

A camera with 100 mm macro lens was used to photograph the mucosal surface of the stomach. The same type of film and identical conditions of specimen distance from the lens, light intensity and film development were used throughout the study. Color slides were evaluated by a computerized image analysis. Each slide was converted to a black-and-white video image consisting of 65,000 points. White represented normal gastric mucosa, while gray or black represented hemorrhagic changes. The value of each point was measured on a digital scale which was based on color intensity and had a range of 0 to 255. Absolute white was given a 255 value while absolute black was given a value of 0. Boundaries delineating the glandular mucosa were drawn on the digital video image with a sonic pen. All spatial and contrast information was stored on a magnetic disk. Each glandular mucosal area was classified interactively by slicing the spectrum of mucosal values into 2 or more subgroups and by displaying the resultant simplified digital image for verification with the more complex analog photographic input. Once a classification scheme was established, a spatial rendition of the picture's point was printed and plotted to scale on paper. A summary of the computer results was also printed and included boundary values for each gray-level slice and the absolute and relative areas of each class. The areas of hemorrhagic changes were expressed as the percentage of the entire gastric glandular mucosal area.

Histological studies

Mucosal specimens 5 mm in width were cut from the forestomach to the pylorus. The specimens were obtained (a) 60 minutes after intragastric administration of 1 ml of solution containing either saline, PL or 120 mM arachidonic acid or (b) 3 hours after intragastric instillation of 2 ml of ethanol in animals which had received 1 ml of solution containing either saline or PL or 120 mM arachidonic acid 1 hours before ethanol. Specimens were fixed in buffered 10% formalin and stained. Coded specimens were examined "blindly" by light microscopy. In the histological evaluation special attention was paid to the continuity of the surface epithelium layer, presence or absence of hemorrhagic erosions, edema of the submucosa and infiltration with polymorphonuclear neutrophils.

Ultrastructural Studies By Scanning Electron Microscopy

Gastric mucosal specimens, fixed in 3.5% buffered glutaraldehyde were processed routinely for scanning electronmicroscopy and evaluated in a JOEL-35 scanning electronmicroscope operated at 20 kV.

Prostaglandin E₂ (PGE₂) Measurements

PGE$_2$ was measured by direct radioimmunoassay using antisera generated in rabbits by immunization of PGE$_2$ linked to bovine thyroglobulin. For additional confirmation of PGE$_2$ measurements, samples were also subjected to bioassay. After addition of approximately 5000 CPM of $^3$H-labeled PGE$_2$ for recovery calculations, samples were adjusted to pH 4.3 with 0.5M phosphate buffer and extracted twice with ethyl acetate. The organic layer was subjected to thin layer chromatography (benzene:dioxane:acetic acid, 90:60:3), and the PGE$_2$ fraction was extracted with methanol, dried and reconstituted in 0.9% NaCl for assay. A bioassay cascade (according to Vane) was used to assay simultaneously the samples in 2 aliquot sizes and on 3 rat stomach strips. The concentration of PGE$_2$ in the gastric contents was measured in 2 groups of rats 30 or 60 minutes following intragastric instillation of 1 ml of 120 mm arachidonic acid or 1 ml PL in order to determine the extent of arachidonic acid conversion to PGE$_2$ by the gastric mucosa. The spontaneous release of PGE$_2$ into the gastric lumen was assessed in animals receiving PL pretreatment only. In addition, PGE$_2$ concentration in the original 120 mM arachidonic acid solution was measured before it intragastric instillation.

RESULTS

Study 1

Pretreatment of animals with saline followed by ethanol administration resulted in severe gastric hemorrhagic lesions. Pretreatment with the PL solubilizer similarly failed to prevent severe mucosal hemorrhagic changes (Table I). In contrast, intragastric pretreatment of rats with 1 ml of 30, 60 and 120 mM arachidonic acid 1 hour prior to the administration of 2 ml of ethanol reduced the development of gastric hemorrhagic lesion in a dose dependent manner (Table I). Pretreatment with 1 ml of 120 mM arachidonic acid either 30 or 60 minutes prior to ethanol instillation protected the gastric mucosa against ethanol injury (Table I).

Study 2

The gastric mucosa of animals which had been pretreated with PL only and 1 hour later had been given 2 ml of ethanol, demonstrated very advanced hemorrhagic changes 15 hours later (Table I). The hemorrhagic changes were seen throughout the fundus, and to a lesser degree in the antrum, and consisted of dark red elongated bands. In contrast, the gastric mucosa of animals which had been pretreated with intragastric instillation of 1 ml of 120 mM arachidonic acid solution 1 hour prior to the instillation of ethanol appeared normal 15 hours later.

Study 3

After the pylorus had been ligated, arachidonic acid was instilled intragastrically or intrajejunally in order to determine whether its protection was a result of local or systemic effects. Intragastric pretreatment with 1 ml of 120 mM arachidonic acid offered significant protection was a result of local or systemic effects. Intragastric pretreatment with 1 ml of 120 mM arachidonic acid offered significant protection of the gastric mucosa against the development of ethanol-induced hemorrhagic lesions (Table I). In contrast, intrajejunal administration of arachidonic acid to animals with ligated pylorus did not protect the gastric mucosa against injury produced by intragastric administration of ethanol (Table I).

Histological changes

Intragastric administration of 1 ml of saline or 5 mM PL did not produce any histological changes. Arachidonic acid installation into the stomach did not change the appearance of the gastric mucosa but did increase the discharge of mucous granules from the surface epithelial cells.

Histologic changes in gastric mucosa 3 hours after ethanol in groups pretreated with PL or arachidonic acid (1 ml of 120 mM) are shown in Table II. Three hours after intragastric installation of 2 ml of ethanol to the animals receiving saline or PL pretreatment, the fundic mucosa showed presence of large areas of mucosal necrosis extending ⅔ to ¾ of the mucosal thickness. These changes occurring in all animals were also present in the glandular mucosa adjacent to the squamous epithelial mucosa of the forestomach, and were characterized by severe congestion of the lamina propria, severe edema of the submucosa, and accumulation of leukocytes in the submucosa and basal lamina propria. Large areas of mucosa were devoid of surface epithelial cells. Sections from macroscopically uninvolved mucosa showed diffuse edema of the submucosa and mucus discharge from the surface epithelial cells.

Mucosal specimens from the stomachs of animals pretreated with arachidonic acid were normal 3 hours after ethanol instillation showing intact surface epithelium with only a few areas of superficial disruption. Some edema of the submucosa and some accumulation of leukocytes were detected. The layer of mucous granules of the surface epithelial cells was thinner and displayed occasional focal defects.

Scanning Electronmicroscopy Results

Rats pretreated with PL showed severe disruption of the mucosal surface and craters of completely denuded lamina propria, at 3 hours after ethanol. In contrast in arachidonic acid pretreated rats 3 hours after ethanol mucosal surface was nondisrupted and normal appearance.

PGE₂ determination

The concentration of PGE$_2$ in gastric content 30 and 60 minutes after intragastric instillation of arachidonic acid or PL are shown in Table III. The values of PGE$_2$ in the gastric content of those animals that received intragastric instillation of arachidonic acid were 5,000–13,000 higher than the values seen in those animals that received intragastric instillation of PL only. The latter values represent the rate of spontaneous release of PGE$_2$ into the gastric lumen. PGE$_2$ was present in the initial arachidonic acid solution (prior to intragastric instillation) in amount equivalent to 0.0027% of the arachidonic acid concentration.

Table I shows the results of the computerized analysis of gastric hemorrhagic areas in respective groups. The results of hemorrhagic mucosal areas are expressed as percent of total gastric glandular mucosal area. In all studies, except group E, ethanol (ETOH) was instilled intragastrically 1 hour after 0.9% NaCl, PL or arachidonic acid (AA). In Group E, ethanol (ETOH) was instilled 30 minutes after arachidonic acid.

TABLE I

| Experiments | Number of Animals | Number of hours after ethanol when stomach evaluated | Hemorrhagic Area* (%) |
|---|---|---|---|
| Study 1 | | | |
| (A) 0.9% NaCL | 4 | 3 | 37.0 |
| (B) PL | 10 | 3 | 33.8 |
| (C) 30 mM AA + PL | 5 | 3 | 15.4 |
| (D) 60 mM AA + PL | 4 | 3 | 3.0 |
| (E) 120 mM AA + PL | 4 | 3 | 0.8 |
| (F) 120 mM AA + PL | 10 | 3 | 0.6 |
| Study 2 | | | |
| (G) PL | 7 | 15 | 27.4 |
| (H) 120 mM AA + PL | 7 | 15 | 0.6 |
| Study 3 | | | |
| (K) 120 mM AA intra-jejunally + PL | 5 | 2 | 28.1 |
| (L) 120 mM AA intra-gastrically + PL | 4 | 2 | 5.3 |
| (M) PL intragastrically | 6 | 2 | 32.2 |

*percent of total glandular mucosal area

TABLE II

Histological changes in gastric mucosa 3 hours after ETOH instillation (2 ml absolute ethanol)

| Group Pretreated With | The Surface Epithelium Layer | Hemorrhagic Erosions | Edema of Submucosa Accumulation of Polymorphonuclears |
|---|---|---|---|
| PL (1 ml) | Disrupted, large area of mucosal surface denuded | Present, multiple penetrating to basal mucosa | Present |
| AA (1 ml 120 mM) + PL | Present, continuous (minor focal defects seen occasionally) | Absent | Present |

TABLE III

Prostaglandin E$_2$ Concentration In Gastric Contents After Intragastric Instillation 1 ml PL or AA (1 ml, 120 mM)

| Groups | PGE$_2$ concentration (ng/ml) | |
|---|---|---|
| | 30 min | 60 min |
| PL | 0.55 ± 0.14 | 0.88 |
| AA | 7360.0* | 4100.0* |

*p < 0.01

Study 4

Linoleic Acid Mucosal Protection

The rats were given intragastric treatment by peroral tube 1 ml of PL solution; 1 ml of the PL solution containing 120 mM linoleic acid (LLC) or 240 mM LLC; or 1 ml of 240 mM oleic acid solubilized in 5 mM PL. One hour after ethanol instillation animals were sacrificed, the stomach was opened along the greater curvature, rinsed with 0.9% NaCl, examined and scored visually and photographed. Macroscopic and histologic mucosal changes were evaluated as in the studies with arachidonic acid.

Results

Rats receiving intragastric pretreatment with PL solution only had 3 hours after ethanol macroscopic hemorrhagic lesions involving 35.8±2% of glandular mucosal area. Treatment with oleic acid did not change significantly occurrence of mucosal hemorrhagic lesions—29.1±3%. Rats receiving pretreatment with 120 mM and 240 mM LLC had significantly decreased macroscopic hemorrhagic lesions—6.5±1% and 1.3±0.5% respectively (p<0.01) 3 hours after ethanol. Macroscopic protection rat gastric mucosa against ethanol was similar to that afforded by arachidonic acid except for the presence of marked edema in the forestomach (containing squamous, paraepidermoidal epithelium) 3 hours after ethanol in group pretreated with linoleic acid (C).

Mucosal Histology

In rats receiving PL or oleic acid pretreatment 3 hours after ethanol deep hemorrhagic necrotic lesions penetrating into muscularis mucosa were present and the continuity of the surface epithelium was disrupted. Three hours after ethanol in animals pretreated with linoleic acid no deep necrotic lesions were present and the surface epithelium was mostly restored with flat or cuboidal immature cells. In the forestomach edema of submucosa was present however.

Study 5

Arachidonic acid mucosal protection against taurocholic acid

Rats were given intragastric treatment by peroral tube with 1 ml of PL solution or 1 ml of PL solution containing 120 mM arachidonic acid (AA). The rats then received, intragastrically, 3 mls of a 80 mM solution of taurocholic acid (TCA) dissolved in 0.1 n HCl, administered twice: one or two hours after PL or AA pretreatment. Animals were sacrificed 3 hours after second TCA administration.

Results

Gastric mucosa was assessed macroscopically and histologically for damage in a similar manner as in studies with ethanol. In PL pretreated animals 3 hours after second does of TCA gastric musoca showed macroscopically presence of linear hemorrhagic lesions occupying 7.5±0.5% of total mucosal area. These lesions corresponding histologically to necrotic lesions were similar to those seen after ethanol. In AA pretreated animals mucosal lesions were not detactable macroscopically and histologically at 3 hours after second TCA dose, proving protective effect of AA against TCA induced gastric mucosal necrosis.

Study 6

Arachidonic and linoleic acid mucosal protection against aspirin

Rats were given intragastric treatment by peroral tube with 1 ml of PL solution, 1 ml of PL solution containing 120 mM arachidonic acid (AA), or 1 ml of PL solution containing 240 mM linoleic acid (LLC). One hour after such treatment a suspension of 200 mg/kg bodyweight of aspirin in 0.1 n HCl containing 1% methyl cellulose was administered intragastrically in 1 ml colume. The animals were sacrificed 4 hours after aspirin administration.

Studies (1) Macroscopic quantitation of mucosal changes based on scoring system estimating presence or absence of hemorrhagic lesions, their number and severity graded on arbitrary scale 1 to 4. Lesion index, expressed as an average score (number of lesions X severity) was estimated per each group of animals.

(2) Mucosal histology
(3) Scanning electron microscopy

Results

Macroscopic mucosal changes at 4 hours after aspirin were 80±6 in the PL group and significantly less (2±0.3 and 8±1) in AA and LLC groups respectively. Histologic evaluation 4 hours after aspirin showed presence of deep necrotic lesions penetrating into midportion of the mucosa in PL pretreated rats. The continuity of the surface epithelium in regions between necrotic leasions was extensively disrupted. In contrast in AA and LLC groups at 4 hours after aspirin deep necrotic lesions did not occur and mucosal surface epithelium was continuous. The scanning electromicroscopy revealed the same findings extensive mucosal damage after aspirin in PL pretreated animals nad nearly normal mucosa in AA and LLC pretreated rats. These studies showed that AA and LLC acid are very effective in protecting rat gastric mucosa against aspirin induced gastric mucosal necrosis.

The compositions of our invention are also effective in healing gastric-duodenal ulceration because of the production of $PGE_2$ which is known to heal such ulceration.

Study 6

40 rats were given, by gavage, either 1 ml of 5 mM PL solution (as a control) or 1 ml of 120 mM arachidonic acid in the 5 mM PL solution. One hour later the rats were given 2.5 ml of 100% ethanol and the animals sacrificed 24 hours later.

The liver was then removed and specimens fixed for 2 hours in 3.5% purified glutaraldehyde (buffered in 0.1M phosphate of 7.4). The liver specimens were washed with buffer and postfixed in 1% osmium tetroxide at 0° C. for 1 hour. After dehydration with graded ethanol the tissue was embed in epoxy resin. Silver gray thin sections of the specimen were double stained with 2% uranyl acetate followed by lead citrate and examined with an RCA electron microscope.

RESULTS

The following ultrastructural changes occured in the hepatocytes of control rats receiving PL solution only followed by 2.5 ml of 100% ethanol (1) focal cytoplasmic necrosis, (2) swelling and irregularity of most of the mitochondria with distrotion of the sized and shape of the cristae, with intramitochondiral dense granules and occasional myelin figures present (3) prominent proliferation and dilatation of the endoplasmic reticulum (4) presence of lipid vacules in the cytoplasm and (5) glycogen depletion and chromatin replacement of most of the nuclear area. These morphological changes were present in all the animals studied. In rats receiving AA pretreatment followed by ethanol, most of the alcohol induced changes were virtually prevented except for lipid vaculization which was significantly reduced.

It is apparent from this example, that a single dose of ethanol administered orally to rats produces prominent ultrastructural changes in the hepatocytes. These changes include alteration of mitochrondria and of cytoplasmic reticulum as well as focal cytoplasmic necrosis (degradation). These changes are similar to those seen in human liver after acute dose alcohol administration.

The present example demonstrated further that oral pretreatment with a single dose of only 37 mg of AA protects the liver against acute injury induced with ethanol.

We claim:
1. A method for protecting or healing injuries of mammalian gastro-duodenal mucosa caused by ethanol, aspirin or taurochalic acid contacting said mucosa, which comprises: orally administrating to said mammals a gastro-duodenal mucosal protective effective amount of an aqueous soluble composition consisting essentially of a fatty acid selected from the group consisting of arachidonic acid and linoleic acid and a pharmaceutically acceptable water solubilizing surface active agent therefor.
2. A method according to claim 1 wherein the fatty acid is arachidonic acid.
3. A method according to claim 1 wherein the fatty acid is linoleic acid.
4. A method according to claim 1 wherein the surface active agent is a non-ionic surface active agent.
5. A method according to claim 4 wherein the non-ionic surface active agent is a polyethenoxy non-ionic surface active agent.

* * * * *